United States Patent [19]

Teller et al.

[11] Patent Number: 4,743,692
[45] Date of Patent: May 10, 1988

[54] N-(PYRIDINYLALKYL)-THIENO-OR BENZO-ISOTHIAZOL-3-AMINE DERIVATIVES

[75] Inventors: Daniel M. Teller, Devon; Donald P. Strike, St. Davids; Arthur A. Santilli, Havertown; Guy A. Schiehser, Malvern, all of Pa.

[73] Assignee: American Home Products Corporation, New York, N.Y.

[21] Appl. No.: 913,876

[22] Filed: Sep. 30, 1986

[51] Int. Cl.[4] ............................................. C07D 513/04
[52] U.S. Cl. .................................. 546/270; 546/256; 544/360; 544/364
[58] Field of Search ............................. 546/270, 256

[56] References Cited

U.S. PATENT DOCUMENTS 4,490,527 12/1984 Schiehser et al. .................. 546/200

FOREIGN PATENT DOCUMENTS 0107914 9/1983 European Pat. Off. .

Primary Examiner—Jane T. Fan
Attorney, Agent, or Firm—Richard K. Jackson

[57] ABSTRACT

A compound of the formula:

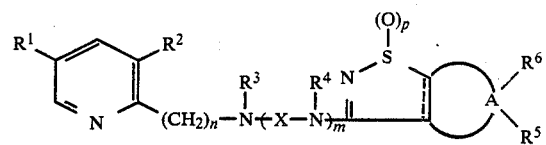

in which

A is a 3,4-; 3,2-; or 2,3-fused thieno- moiety or a benzo- moiety;

X is alkylene of 2 to 5 carbon atoms;

$R^1$ is hydrogen, bromo or methyl;

$R^2$ is methoxy when $R^1$ is hydrogen, methyl when $R^1$ is bromo, and bromo when $R^1$ is methyl;

$R^3$ is hydrogen or alkyl of 1 to 6 carbon atoms;

$R^4$ is hydrogen or alkyl of 1 to 6 carbon atoms;

$R^3$ and $R^4$, taken together, are ethylene when X is ethylene;

$R^5$ is hydrogen when A is thieno, and when A is benzo, $R^5$ is hydrogen, alkyl of 1 to 6 carbon atoms, halo or alkoxy of 1 to 6 carbon atoms;

$R^6$ is hydrogen when A is thieno, and when A is benzo, $R^5$ is hydrogen, alkyl of 1 to 6 carbon atoms, halo, alkoxy of 1 to 6 carbon atoms, amino, nitro, sulfamoyl or pyridinyl;

m is one of the integers 0 or 1;

n is one of the integers 3, 4 or 5;

p is one of the integers 0, 1 or 2; and the dotted line in the thiazole ring represents unsaturation necessary to complete the 3,2- or 2,3- thieno-ring;

or a pharmaceutically acceptable salt thereof are histamine $H_1$-antagonists useful in the treatment of various allergic reactions in the mammal.

14 Claims, No Drawings

N-(PYRIDINYLALKYL)-THIENO- OR BENZO-ISOTHIAZOL-3-AMINE DERIVATIVES

BACKGROUND OF THE INVENTION

A group of histamine $H_1$-antagonists discovered by George S. Sach are disclosed in European patent application No. 107,914 as aminopyrimidinone derivatives which may be depicted as:

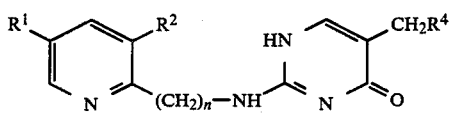

wherein $R^1$ is halogen, nitro, amino or alkyl; $R^2$ is halogen, nitro, amino, alkyl or alkoxy, $R^4$ is phenyl or substituted phenyl where the substituent may be halo, hydroxy, alkyl, alkoxy or methylenedioxy and n is 3–5.

Schiehser et al., U.S. Pat. No. 4,490,527, discloses a series of histamine $H_2$-antagonists which are thieno- or benzo-isothiazole amines N-substituted by an aryloxyalkyl group or moieties common to ranitidine and tiotidine.

DESCRIPTION OF THE INVENTION

In accordance with this invention, there is provided a group of antihistamine agents of the formula:

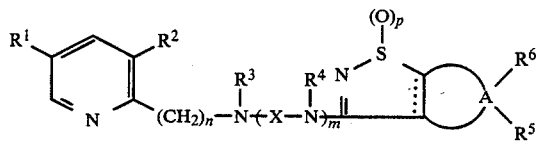

in which
A is a 3,4-; 3,2-; or 2,3-fused thieno-moiety or a benzo-moiety;
X is alkylene of 2 to 5 carbon atoms;
$R^1$ is hydrogen, bromo or methyl;
$R^2$ is methoxy when $R^1$ is hydrogen, methyl when $R^1$ is bromo, and bromo when $R^1$ is methyl;
$R^3$ is hydrogen or alkyl of 1 to 6 carbon atoms;
$R^4$ is hydrogen or alkyl of 1 to 6 carbon atoms;
$R^3$ and $R^4$, taken together, are ethylene when X is ethylene;
$R^5$ is hydrogen when A is thieno, and when A is benzo, $R^5$ is hydrogen, alkyl of 1 to 6 carbon atoms, halo or alkoxy of 1 to 6 carbon atoms;
$R^6$ is hydrogen when A is thieno, and when A is benzo, $R^5$ is hydrogen, alkyl of 1 to 6 carbon atoms, halo, alkoxy of 1 to 6 carbon atoms, amino, nitro, sulfamoyl or pyridinyl;
m is one of the integers 0 or 1;
n is one of the integers 3, 4 or 5;
p is one of the integers 0, 1 or 2; and
the dotted line in the thiazole ring represents unsaturation necessary to complete the 3,2- or 2,3-thieno-ring;
or a pharmaceutically acceptable salt thereof.

The preferred thienoisothiazolamine derivatives present a group of compounds of the formula:

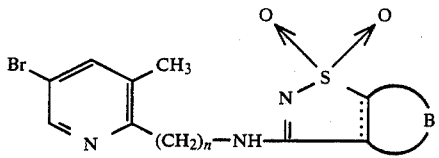

in which B is

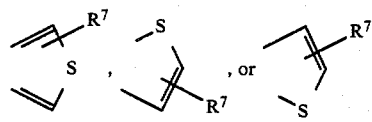

$R^7$ is hydrogen, alkyl of 1 to 6 carbon atoms; halo, alkoxy of 1 to 6 carbon atoms; amino, nitro or sulfamoyl; and
n is one of the integers 3, 4 or 5;
or a pharmaceutically acceptable salt thereof.

The preferred benzoisothiazolamine derivatives present a group of compounds of the formula:

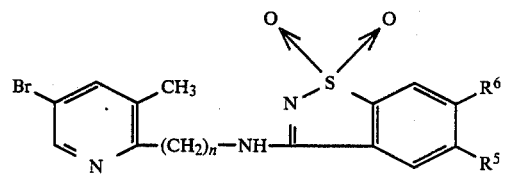

in which
$R^5$ is hydrogen, halo or alkoxy of 1 to 6 carbon atoms;
$R^6$ is hydrogen, halo, nitro, amino, sulfamoyl or pyridinyl; and
n is one of the integers 3, 4 or 5;
or a pharmaceutically acceptable salt thereof.

The pharmaceutically acceptable salts of the antihistamine agents of this invention are prepared by conventional means with inorganic or organic acids such as hydrochloric, hydrobromic, sulfuric, phosphoric, nitric, acetic, fumaric, citric, tartaric, maleic, lactic, 2-hydroxyethanesulfonic, methanesulfonic, toluene-4-sulfonic, ethanesulfonic, and the like.

The compounds of this invention are prepared by methods generally known in the art. Displacement of the methylthio substituent on a 3-methylthio-thienoisothiazole by an appropriately substituted 2-pyridinylalkylamine yields the desired thienoisothiazoles while displacement of the halo-substituent on an appropriately substituted 3-halo benzoisothiazole by the 2-pyridinylalkylamines affords the desired benzoisothiazole derivatives.

The compounds of this invention were established to be histamine $H_1$-receptor antagonists useful in the treatment of various allergic reactions of the mammal by subjecting them to the following standard test for $H_1$-blocking activity:

Fresh segments of terminal ileum immediately proximal to Peyer's patch, obtained from male Buckshire guinea pigs, were suspended in 37° C. Tyrode's solution in a tissue bath and aerated. The tissue segments were placed under one gram tension and allowed to equilibrate for one hour. Histamine was added to each tissue bath to a final concentration of $1 \times 10^{-7}$M. The response was noted as grams tension. Test drug was added, in the presence of histamine, to each bath to a final concentration of $1\times10^{-6}$M. The change in grams tension was noted and the percent reduction in grams tension calculated. The results of this study are presented in conjunction with the example of each compound's production, infra.

The pharmacological results obtained characterize the compounds of this invention as $H_1$-receptor antagonists useful in the treatment of conditions such as asthma, hay fever, allergic rhinitis and eczema. As such, they may be administered topically or systemically. Topical administration is advantageously achieved to the skin via creams, ointments or lotions or via aerosol introduction into the respiratory tract. Systemic administration may be orally, parenterally or rectally. In each instance, conventional formulations amenable to use in the desired administration route is appropriate. Hence, tablets and capsules may be prepared for oral administration, suppositories for rectal administration and isotonic aqueous solutions for intravenous, subcutaneous or intramuscular injection.

As is conventional in the case of antihistaminic agents, the appropriate dosage is determined on a subjective basis by initial administration of small amounts, ca. 1–15 mg. followed by increasing quantities up to about 500 mg. topical, oral or rectal and about 200 mg. intraveneous, until the desired symptomatic relief is obtained. The dosage is personalized in this manner for each patient, based upon size, age, type of discomfort, degree of disability, etc. by the physician.

The following examples are presented to illustrate the preparation of a representative number of compounds embraced by this invention.

EXAMPLE 1

N-[4-(5-bromo-3-methyl-2-pyridinyl)butyl]thieno[3,4-d]isothiazol-3-amine 1,1-dioxide To a solution of 4-(5-bromo-3-methyl-2-pyridinyl)butylamine (Australia No. 12847/83) (2.115 g, 9.027 mmoles) in absolute ethanol (57 ml) is added 3-(methylthio)thieno[3,4-d]isothiazole-1,1-dioxide (U.S. Pat. No. 4,490,527) (1.980 g, 9.027 mmoles) neat in one portion. The resulting slurry is heated in an oil bath to 58° C. where more absolute ethanol (9 ml) is added to give complete solution. The temperature is raised to reflux and held there for one hour. After standing for two hours at room temperature, the precipitate which forms is filtered to give 2.891 g of the crude free base. Recrystallization from acetonitrile gives the purified free base, 2.339 g colorless solid, m.p.=210°–212° C. Treatment of 2.20 g of the purified free base with isopropanolic hydrogen chloride and subsequent recrystallization from $CH_3OH/CH_2Cl_2$/2-propanol gives 1.700 g of the HCl salt of the title compound: m.p. 238°–250° C., IR (KBr) 3075, 1985, 1602, 1305, 1152 cm$^{-1}$. $^1$H NMR (Me$_2$SO-d$_6$) 9.71 (1H, t), 8.67 (1H, s), 8.38 (1H, d), 8.31 (1H, s), 8.24 (1H, d), 6.15 (broad), 3.42 (2H, m), 2.94 (2H, m), 2.40 (3H, s), 1.73 (4H, m).

Analysis for: $C_{15}H_{16}BrN_3O_2S_2\cdot HCl$. Calculated: C, 39.97; H, 3.80; N, 9.32; Br, 17.73; Cl, 7.86. Found: C, 40.35; H, 3.73; N, 9.11; Br, 17.24; Cl, 7.77.

Percent reduction: 81%.

EXAMPLE 2

N-[4-(5-bromo-3-methyl-2-pyridinyl)butyl]thieno[2,3-d]isothiazol-3-amine 1,1-dioxide To a stirred solution of 15.2 g (0.08 mole) of 2,3-dihydro-3-oxothieno[2,3-d]isothiazole 1,1-dioxide (U.S. Pat. No. 4,028,373) in 200 ml of dry pyridine at 80° C. was added 15.2 g of phosphorus pentasulfide over a period of 10 minutes. The reaction mixture was stirred for a period of 45 minutes at this temperature and was then poured into 500 ml of ice water. The reaction mixture was acidified with conc. hydrochloric acid solution to pH 1. The resulting precipitate was collected on a filter and was dissolved in 20% sodium bicarbonate solution then filtered. The filtrate upon acidification with conc. hydrochloric acid gave 7.6 g of thieno[2,3-d]isothiazole-3(2H)-thione 1,1-dioxide, m.p. 185°–187° C. A second treatment of the precipitate which did not dissolve with 20% sodium bicarbonate followed by acidification gave an additional 3.7 g of product, m.p. 186°–189° C. The two crops of product were combined giving 11.3 g (69%).

Analysis for: $C_5H_3NO_2S_3$. Calculated: C, 29.26; H, 1.47; N, 6.82. Found: C, 29.47; H, 1.82; N, 6.35.

To a stirred solution of 11.3 g (0.055 mole) of thieno[2,3-d]isothiazole-3(2H)-thione 1,1-dioxide in 100 ml of acetone containing 4.63 g (0.055 mole) of sodium bicarbonate was added 15.6 g (0.11 mole) of methyl iodide. The reaction mixture was heated overnight under reflux, filtered and the solvent was removed in vacuo. The product, 3-(methylthio)thieno[2,3-d]isothiazole 1,1-dioxide, amounted to 10.1 g, m.p. 165°–167° C.

Analysis for: $C_6H_5NO_2S_3$. Calculated: C, 32.86; H, 2.30; N, 6.39. Found: C, 32.85; H, 2.33; N, 6.25.

A mixture of 0.514 g (0.0021 mole) of 4-(5-bromo-3-methyl-2-pyridinyl)butylamine and 0.463 g (0.0021 mole) of 3-(methylthio)thieno[2,3-d]isothiazole 1,1-dioxide in 35 ml of ethanol was heated under reflux with stirring for 4 hours. The reaction solution was cooled in ice giving a crystalline product which amounted to 0.71 g, m.p. 191°–193° C.

Analysis for: $C_{15}H_{16}BrN_3O_2S_2$. Calculated: C, 43.48; H, 3.89; N, 10.14. Found: C, 43.63; H, 3.91; N, 10.01.

Percent reduction: 73%

EXAMPLE 3

N-[4-(5-bromo-3-methyl-2-pyridinyl)butyl]-1,2-benzisothiazol-3-amine 1,1-dioxide To a refluxing solution of 4-(5-bromo-3-methyl-2-pyridinyl)butylamine (1.87 g, 7.69 mmol) in chloroform (80 ml, freed of EtOH by passage through Woelm Grade I neutral alumina) was added over 50 minutes a solution of 3-chloro-1,2-benzisothiazole-1,1-dioxide (U.S. Pat. No. 4,490,527) (1.55 g, 7.69 mmol) in chloroform (50 ml, purified as above) while maintaining reflux. After the addition was complete, reflux was continued for another 15 minutes. Evaporation in vacuo gave a yellow orange foam. Crystallization from 2-propanol and recrystallization from methanol/methylene chloride/2-propanol (Norite) gave 2.07 g of the title compound as a tan solid hydrochloride: m.p. 232°–244° C., IR(KBr) 3070, 1610, 1578, 1508, 1280, 1140 cm$^{-1}$. $^1$H NMR (Me$_2$SO d$_6$) 9.85 (1H, t), 8.70 (1H, s), 8.33 (1H, m), 8.27 (1H, s), 7.88 (3H, m) 3.40 (2H, m), 2.90 (2H, m), 2.37 (3H, s), 1.70 (4H, m).

Analysis for: $C_{17}H_{18}BrN_3O_2S\cdot HCl$. Calculated: C, 45.91; H, 4.30; N, 9.45; Br, 17.97; Cl, 7.97. Found: C, 45.82; H, 4.35; N, 9.42; Br, 17.71; Cl, 7.86.

Percent reduction: 86%.

EXAMPLE 4

N-[4-(5-bromo-3-methyl-2-pyridinyl)butyl]-5-chloro-1,2-benzisothiazol-3-amine 1,1-dioxide To a refluxing solution of 4-(5-bromo-3-methyl-2-pyridinyl)butylamine (300 mg, 1.23 mmol) in chloroform (20 ml, purified as in previous example) was added over 10 minutes a solution of 3,5-dichloro-1,2-benzisothiazole 1,1-dioxide (U.S. Pat. No. 4,490,527) (400 mg, 1.69 mmol) in chloroform (20 ml)/acetonitrile (10 ml). Since a precipitate formed during the addition, another 10 ml of acetonitrile was added to give almost complete solution. Heating at 65°–70° C. was continued for 60 minutes giving a slightly cloudy mixture. Cooling to room temperature, filtration and evaporation of the filtrate in vacuo gave a solid residue. Recrystallization from methanol/methylene chloride/2-propanol gave 0.410 g of the title compound as an off-white solid hydrochloride: m.p. 231°–235° C., IR(KBr) 3005, 2500 (broad), 1620, 1278, 1160 cm$^{-1}$. $^1$H NMR (Me$_2$SO-d$_6$) 9.87 (1H, t), 8.68 (1H, s), 8.60 (1H, s), 8.25 (1H, s), 7.90 (2H, m), 3.42 (2H, m), 2.83 (2H, m), 2.37 (3H, s), 1.68 (4H, m).

Analysis for: $C_{17}H_{17}BrClN_3O_2S \cdot HCl$. Calculated: C, 42.61; H, 3.79; N, 8.77; Br, 16.67; Cl, 14.80. Found: C, 42.97; H, 3.76; N, 8.54; Br, 16.91; Cl, 15.40.

Percent reduction: 58%.

EXAMPLE 5

N-[4-(5-bromo-3-methyl-2-pyridinyl)butyl]-5-methoxy-1,2-benzisothiazol-3-amine 1,1-dioxide To 4-(5-bromo-3-methyl-2-pyridinyl)butylamine (0.375 g, 1.54 mmol) dissolved by heating in acetonitrile (20 ml) and maintained at 57°–58° C. was added over 5 minutes under nitrogen a solution of 3-chloro-5-methoxy-1,2-benzisothiazole 1,1-dioxide (U.S. Pat. No. 4,490,527) (0.500 g, 2.16 mmol) in acetonitrile (10 ml). After 1¾ hours at 57°–58° C., cooling to room temperature and filtering gave 0.439 g colorless precipitate. The precipitate was dissolved in methylene chloride/sat. aq. sodium bicarbonate. Extraction of the aqueous layer with methylene chloride, combination of the extracts with the organic layer, washing with brine, drying over anhydrous magnesium sulfate, filtration and evaporation in vacuo gave a colorless solid. Column chromatography on silica gel and recrystallization from ethyl acetate gave 0.176 g of the title compounds as colorless solid: m.p. 161°–162° C., IR(KBr) 3280, 1610, 1583, 1528, 1278, 1240, 1157, 1120 cm$^{-1}$. $^1$H NMR (Me$_2$SO-d$_6$) 9.18 (1H, m), 7.84 (1H, s), 7.69 (2H, m), 7.25 (1H, d), 3.89 (3H, s), 3.46 (2H, m), 2.68 (2H, m), 2.24 (3H, s), 1.63 (4H, m).

Analysis for: $C_{18}H_{20}BrN_3O_3S$. Calculated: C, 49.32; H, 4.60; N, 9.59; Br, 18.23. Found: C, 49.36; H, 4.59; N, 9.60; Br, 17.83.

Percent reduction: 75%.

EXAMPLE 6

3-[[4-(5-bromo-3-methyl-2-pyridinyl)butyl]amino]-1,2-benzisothiazole-6-sulfonamide 1,1-dioxide A mixture of 4-(5-bromo-3-methyl-2-pyridinyl)butylamine (336 mg, 1.38 mmol) and 3-thiomethyl-6-sulfamoyl benzoisothiazole 1,1-dioxide (U.S. Pat. No. 4,490,527) (425 mg, 1.45 mmole) was dissolved in 20 ml acetonitrile under dry nitrogen and stirred for 45 minutes, during which time the title compound precipitated, giving 529 mg (78.6%), m.p. 219°–221° C. IR(KBr) 3320, 1625, 1348, 1290, 1175, 1150, 1135 cm$^{-1}$.

Analysis for: $C_{17}H_{19}BrN_4O_4S_2$. Calculated: C, 41.89; H, 3.93; N, 11.49. Found: C, 41.88; H, 3.81; N, 11.42.

Percent reduction: 63%.

EXAMPLE 7

N-[4-(5-bromo-3-methyl-2-pyridinyl)butyl]-6-nitro-1,2-benzisothiazol-3-amine 1,1-dioxide A mixture of 4-(5-bromo-3-methyl-2-pyridinyl)butylamine (318 mg, 1.31 mmol) and 3-chloro-6-nitrobenzisothiazole 1,1-dioxide (U.S. Pat. No. 4,490,527) (357 mg, 1.45 mmol) in 15 ml acetonitrile was stirred under dry nitrogen at room temperature then heated to reflux for several minutes until the material dissolved. The solvent was removed under reduced pressure and the residue recrystallized from ethanol and triturated with hot ethanol, yielding 250 mg (39%) of the title compound as the hydrochloride salt, m.p. 235°–242° C. IR(KBr) 1620, 1345, 1300, 1160 cm$^{-1}$.

Analysis for: $C_{17}H_{18}BrCln_4O_4S$. Calculated: C, 41.69; H, 3.70; N, 11.44. Found: C, 41.82; H, 3.81; N, 11.33.

Percent reduction: 52%.

EXAMPLE 8

6-bromo-N-[4-(5-bromo-3-methyl-2-pyridinyl)butyl]-1,2-benzisothiazol-3-amine 1,1-dioxide A slurry of 4-(5-bromo-3-methyl-2-pyridinyl)butylamine (252 mg, 1.04 mmol) and 6-bromo-3-chlorobenzisothiazole 1,1-dioxide (U.S. Pat. No. 4,490,527) (292 mg, 1.04 mmol) in 15 ml acetonitrile was heated under dry nitrogen until nearly completely dissolved, when the above compound precipitated as the hydrochloride salt, yielding 360 mg (66%), m.p. 224°–232° C. IR(KBr) 1620, 1300, 1160, 650 cm$^{-1}$.

Analysis for: $C_{17}H_{18}Br_2ClN_3O_2S$. Calculated: C, 38.99; H, 3.46; N, 8.02. Found: C, 38.97; H, 3.50; N, 8.41.

Percent reduction: 77%.

EXAMPLE 9

N$^3$-[4-(5-bromo-3-methyl-2-pyridinyl)butyl]-1,2-benzisothiazol-3,6-diamine 1,1-dioxide N-[4-(5-bromo-3-methyl-2-pyridinyl)butyl]-6-nitro-1,2-benzisothiazol-3-amine 1,1-dioxide (780 mg, 1.72 mmol) was dissolved in 200 ml ethanol and shaken on a Parr pressure reaction apparatus with 5% palladium on carbon (120 mg) under hydrogen at an initial pressure of 53 lb.in$^{-2}$ until hydrogen uptake stopped. The catalyst was removed by filtration and the ethanol was removed under reduced pressure. The resulting brown solid was triturated with hot ethyl acetate and the product was separated from impurities by high pressure liquid chromatography using equal volumes of ethyl acetate and methylene chloride as eluent. Evaporation of the solvent under reduced pressure left the above compound as a white solid monoethyl acetate solvate (132 mg, 15%), m.p. 276°–279° C. IR(KBr) 3290, 1731, 1615, 1130 cm$^{-1}$.

Analysis for: $C_{21}H_{27}BrN_4O_4S$. Calculated: C, 49.32; H, 5.32; N, 10.95. Found: C, 48.81; H, 4.95; N, 11.08.

Percent reduction: 84%.

EXAMPLE 10

N-[4-(5-bromo-3-methyl-2-pyridinyl)butyl]-6-(2-pyridinyl)-1,2-benzisothiazol-3-amine 1,1-dioxide To 50 g (0.3 mol) of 2(4-methylphenyl)pyridine cooled to 0° C. is added dropwise 140 g. (1.2 mol, 80 ml) of chlorosulfonic acid. The reaction mixture is heated to 115° C. and is maintained for 1 hour.

The reaction mixture is cooled in ice and then is added to cracked ice/ice water. The resulting white solid is separated by suction filtration. The solid is added to a mixture of 250 ml of concentrated ammonia hydroxide and 250 ml of ethyl ether. After agitation, the mixture is filtered and the filtrate evaporated to give 18.5 g of crude product. Trituration with cyclohexane gave a solid which is partitioned between water:ammonium hydride (1:1) and ethyl acetate. The organic extract is dried (MgSO$_4$), filtered and rotoevaporated to give 2-methyl-5-(2-pyridinyl)-benzenesulfonamide, m.p. 173°–176° C.

Analysis for: $C_{12}H_{12}N_2O_2S$. Calculated: C, 58.04; H, 4.87; N, 11.28. Found: C, 57.55; H, 4.90; N, 11.16.

2-methyl-5-(2-pyridinyl)-benzenesulfonamide (7.44 g, 30 mmol) is dissolved in a solution of 3.0 g (75 mmol) of sodium hydroxide in 60 ml of water. The resulting solution is heated to 80° C. and then potassium permanganate (15.0 g, 90 mmol) is added portionwise over 1 hour.

The reaction mixture is treated with isopropyl alcohol and is filtered through Celite. The solution is treated with hydrochloric acid and the resulting precipitate is filtered and dried to give crude title compound. An analytical sample is prepared by refluxing and crude product with trifluoroacetic anhydride and dissolving the product in aqueous sodium bicarbonate. Precipitation with 5N aqueous hydrochloric acid, filtration and drying gives 6-(2-pyridinyl)-1,2-benzisothiazol-3-ol 1,1-dioxide: m.p. 305°–311° C.

Analysis for: $C_{12}H_8N_2O_3S$. Calculated: C, 55.37; H, 3.10; N, 10.77. Found: C, 54.59; H, 3.28; N, 10.78.

A mixture of 6-(2-pyridinyl)-1,2-benzisothiazolin-3-one 1,1-dioxide (0.390 g, 1.57 mmol) and phosphorus pentachloride (0.397 g, 1.91 mmol) in diglyme (3.75 ml) was heated to 150° C. in an oil bath to give 3-chloro-6-(2-pyridinyl)-1,2-benzisothiazole-1,1-dioxide. After allowing the temperature to fall to 90° C., acetonitrile (15 ml) was added and then 4-(5-bromo-3-methyl-2-pyridinyl)butylamine (0.503 g, 2.07 mmol) neat in one portion. Heating at 90°–95° C. was continued for three hours during which time a heavy precipitate formed. After coming to room temperature the mixture was filtered to give 0.530 g of a tan solid. Shaking with a mixture of methylene chloride and sat. aq. sodium bicarbonate, separation of the organic layer, extraction of the organic layer with methylene chloride, combination of the organic layers and extracts, drying over anhydrous magnesium sulfate, filtration and evaporation in vacuo gave the free base. Column chromatography on silica gel and recrystallization from methanol/methylene chloride/2-propanol gave 0.267 g of the title compound as a tan solid: m.p. 233°–234° C., IR(KBr) 3270, 1612, 1580, 1455, 1279, 1142, 1120 cm$^{-1}$. $^1$H NMR (Me$_2$SO d$_6$) 9.45 (1H, m), 8.80 (1H, d), 8.72 (1H, s), 8.67 (1H, d), 8.50 (1H, d), 8.38 (1H, d), 8.35 (1H, d), 8.04 (1H, t), 7.88 (1H, s), 7.57 (1H, m), 3.57 (2H, t), 2.69 (2H, t), 2.31 (3H, s), 1.83 (4H, m).

Analysis for: $C_{22}H_{21}BrN_4O_2S$. Calculated: C, 54.44; H, 4.36; N, 11.54; Br, 16.46. Found: C, 54.04; H, 4.32; N, 11.52; Br, 16.49.

Percent reduction: 98%.

EXAMPLE 11

N-[4-(5-bromo-3-methyl-2-pyridinyl)butyl-N'-(thieno[3,4-d]isothiazol-3-yl)-1,2-ethane diamine S,S-dioxide A mixture of 0.61 g (0.01 mole) of aminoethanol and 2.19 g (0.01 mole) of 3-(methylthio)thieno[3,4-d]isothiazole 1,1-dioxide in 35 ml of ethanol was heated under reflux overnight and then cooled in ice. There was obtained 2.2 g of 2-[(thieno[3,4-d]isothiazol-3-yl)amino]ethanol S,S-dioxide, m.p. 245°–246° C. An analytical sample was obtained by recrystallization from ethanol, m.p. 252°–254° C.

Analysis for: $C_7H_8N_2O_3S_2$. Calculated: C, 36.19; H, 3.47; N, 12.06. Found: C, 36.48; H, 3.47; N, 11.62.

To an ice-cooled solution of 2.1 g (0.009 mole) of 2-[thieno[3,4-d]isothiazol-3-yl)amino]ethanol S,S-dioxide in 20 ml of dry pyridine was added in portions 1.72 g (0.009 mole) of p-toluenesulfonyl chloride. After allowing the reaction mixture to stand at room temperature for 1½ hours it was poured into 300 ml of water. The crystalline product 2-[(thieno[3,4-d]isothiazol-3-yl)amino]ethanol S,S-dioxide 4-methylbenzenesulfonate(ester) was obtained, m.p. 174°–179° C. and used directly in the next step.

Analysis for: $C_{14}H_{14}N_2O_5S_3$. Calculated: C, 43.51; H, 3.65; N, 7.25. Found: C, 43.30; H, 3.67; N, 7.26.

A solution of 1.46 g (0.006 mole) of 4-(5-bromo-3-methyl-2-pyridinyl)butylamine and 2.32 g (0.006 mole) of 2-[(thieno[3,4-d]isothiazol-3-yl)amino]ethanol s,s-dioxide 4-methylbenzenesulfonate(ester) in 70 ml of anhydrous ethanol was heated under reflux overnight. The reaction mixture was evaporated to dryness in vacuo. The residue was subjected to HPLC using a silica prep pack (98 percent methanol, 2 percent ammonium hydroxide). Two fractions when combined and evaporated gave 0.13 g of N-[4-(5-bromo-3-methyl-2-pyridinyl)butyl]-N$^1$-(thieno[3,4-d]isothiazol-3-yl)-1,2-ethanediamine s,s-dioxide, m.p. 132°–136° C.

Analysis for: $C_{17}H_{21}BrN_4O_2S_2$. Calculated: C, 44.64; H, 4.63; N, 12.21. Found: C, 44.65; H, 4.57; N, 11.70.

Percent Reduction: 32%.

What is claimed is:

1. A compound of formula:

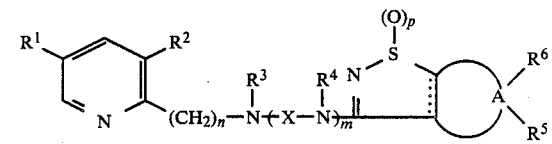

in which

A is a 3,4-; 3,2-; or 2,3-fused thieno-moiety or a benzo-moiety;

X is alkylene of 2 to 5 carbon atoms;

R$^1$ is hydrogen, bromo or methyl;

R$^2$ is methoxy when R$^1$ is hydrogen, methyl when R$^1$ is bromo, and bromo when R$^1$ is methyl;

R$^3$ is hydrogen or alkyl of 1 to 6 carbon atoms;

R$^4$ is hydrogen or alkyl of 1 to 6 carbon atoms;

$R^5$ is hydrogen when A is thieno, and when A is benzo $R^5$ is hydrogen, alkyl of 1 to 6 carbon atoms, halo or alkoxy of 1 to 6 carbon atoms;

$R^6$ is hydrogen when A is thieno, and when A is benzo $R^5$ is hydrogen, alkyl of 1 to 6 carbon atoms, halo, alkoxy of 1 to 6 carbon atoms, amino, nitro, sulfamoyl or pyridinyl;

m is one of the integers 0 or 1;

n is one of the integers 3, 4 or 5;

p is one of the integers 0, 1 or 2; and the dotted line in the thiazole ring represents unsaturation necessary to complete the 3,2- or 2,3- thieno- ring;

or a pharmaceutically acceptable salt thereof.

2. A compound of claim 1 of the formula:

[structure]

in which $R^5$ is hydrogen, halo or alkoxy of 1 to 6 carbon atoms;

$R^6$ is hydrogen, halo, nitro, amino, sulfamoyl or pyridinyl; and n is one of the integers 3, 4 or 5;

or a pharmaceutically acceptable salt thereof.

3. A compound of claim 1 of the formula:

[structure]

in which B is

[structures]

$R^7$ is hydrogen, alkyl of 1 to 6 carbon atoms, halo, alkoxy of 1 to 6 carbon atoms; amino, nitro or sulfamoyl; and n is one of the integers 3, 4 or 5;

or a pharmaceutically acceptable salt thereof.

4. The compound of claim 1 which is N-[4-(5-bromo-3-methyl-2-pyridinyl)butyl]thieno[3,4-d]isothiazol-3-amine 1,1-dioxide or a pharmaceutically acceptable salt thereof.

5. The compound of claim 1 which is N-[4-(5-bromo-3-methyl-2-pyridinyl)butyl]thieno[2,3-d]isothiazol-3-amine 1,1-dioxide or a pharmaceutically acceptable salt thereof.

6. The compound of claim 1 which is N-[4-(5-bromo-3-methyl-2-pyridinyl)butyl]-1,2-benzisothiazol-3-amine 1,1-dioxide or a pharmaceutically acceptable salt thereof.

7. The compound of claim 1 which is N-[4-(5-bromo-3-methyl-2-pyridinyl)butyl]-5-chloro-1,2-benzisothiazol-3-amine 1,1-dioxide or a pharmaceutically acceptable salt thereof.

8. The compound of claim 1 which is N-[4-(5-bromo-3-methyl-2-pyridinyl)butyl]-5-methoxy-1,2-benzisothiazol-3-amine 1,1-dioxide or pharmaceutically acceptable salt thereof.

9. The compound of claim 1 which is 3-[[4-(5-bromo-3-methyl-2-pyridinyl)butyl]amino]-1,2-benzisothiazole-6-sulfonamide 1,1-dioxide or a pharmaceutically acceptable salt thereof.

10. The compound of claim 1 which is N-[4-(5-bromo-3-methyl-2-pyridinyl)butyl]-6-nitro-1,2-benzisothiazol-3-amine 1,1-dioxide or a pharmaceutically acceptable salt thereof.

11. The compound of claim 1 which is 6-bromo-N-[4-(5-bromo-3-methyl-2-pyridinyl)butyl]-1,2-benzisothiazol-3-amine 1,1-dioxide or a pharmaceutically acceptable salt thereof.

12. The compound of claim 1 which is $N^3$-[4-(5-bromo-3-methyl-2-pyridinyl)butyl]-1,2-benzisothiazol-3,6-diamine 1,1-dioxide or a pharmaceutically acceptable salt thereof.

13. The compound of claim 1 which is N-[4-(5-bromo-3-methyl-2-pyridinyl)butyl]-6-(2-pyridinyl)-1,2-benzisothiazol-3-amine 1,1-dioxide or a pharmaceutically acceptable salt thereof.

14. The compound of claim 1 which is N-[4-(5-bromo-3-methyl-2-pyridinyl)butyl]-N'-(thieno[3,4-d]isothiazol-3-yl)-1,2-ethane diamine S,S-dioxide, or a pharmaceutically acceptable salt thereof.

* * * * *